United States Patent [19]

Brattesani

[11] 4,120,862
[45] Oct. 17, 1978

[54] USE OF COPPER HALIDE CATALYSTS AND CERTAIN EPOXY COMPOUNDS TO OXIDIZE NITRO-SUBSTITUTED SCHIFF BASES TO BENZOXAZOLES

[75] Inventor: Donald N. Brattesani, Oakland, Calif.

[73] Assignee: The Dow Chemical Company, Midland, Mich.

[21] Appl. No.: 827,649

[22] Filed: Aug. 25, 1977

[51] Int. Cl.² .................................... C07D 263/56
[52] U.S. Cl. .................. 260/307 D; 260/566 F; 423/DIG. 14
[58] Field of Search .................... 260/307 D

[56] References Cited

U.S. PATENT DOCUMENTS 4,020,081   4/1977   MacKay et al. ................ 260/307 D

OTHER PUBLICATIONS

Stephens et al. (I)–J. Chem. Soc. 2791 (1949).
Stephens et al. (II)–J. Chem. Soc. 1722 (1950).

Primary Examiner—Raymond V. Rush
Attorney, Agent, or Firm—R. R. Stringham

[57] ABSTRACT

The combination of a copper halide catalyst certain peroxidic compounds has been found advantageous for the oxidation of Schiff bases of the formula

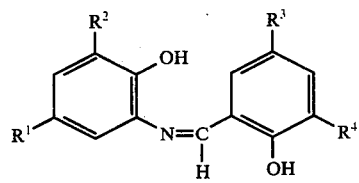

to the corresponding benzoxazoles

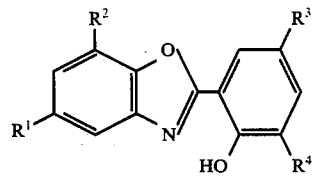

wherein one of $R^3$ and $R^4$ is $-NO_2$ and the other is $-H$, alkyl of 1 to 20 carbons, or $-NO_2$; and $R^1$ and $R^2$ are independently $-H$ or alkyl of 1 to 20 carbons, with the proviso that $R^1$, $R^2$, $R^3$ and $R^4$ contain a total of 6 carbons. Benzoxazoles of the latter type have utility as organo-soluble, metallurgical extractants.

10 Claims, No Drawings

USE OF COPPER HALIDE CATALYSTS AND CERTAIN EPOXY COMPOUNDS TO OXIDIZE NITRO-SUBSTITUTED SCHIFF BASES TO BENZOXAZOLES

BACKGROUND OF THE INVENTION

A novel group of oil-soluble, acidic benzoxazoles has utility as metallurgical extractants. These benzoxazoles are defined by the formula

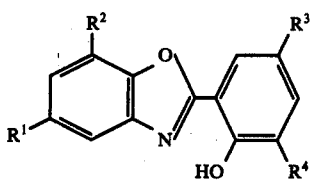

wherein one of $R^3$ and $R^4$ is $-NO_2$ and the other is $-H$, $-NO_2$ or an alkyl group of 1 to 20 carbons; and $R^1$ and $R^2$ are $-H$ or an alkyl group of 1 to 20 carbons independently, but with the proviso that $R^1$, $R^2$, $R^3$ and $R^4$ contain a total of at least 6 carbons.

The hydrocarbyl substituents on the benzoxazole molecule must contain a total of 6 to provide the requisite solubility of the metal complexes in extraction solvents such as kerosene. The presence of at least one nitro group, ortho or para to the phenolic hydroxyl, makes the benzoxazole sufficiently acidic to be useful for extraction of metal ions from unneutralized ore-leaches, i.e., leaches having pH's of about 2 or less. The presence of the nitro group (s) also appears to be responsible for an enhanced selectivity for copper over iron.

Several methods of making benzoxazoles are known. For example, U.S. Pat. No. 4,020,081 discloses metallurgical extractants consisting of benzoxazoles which are similar to those of the above formula but contain no nitro groups. They are made by condensation of salicylamides with aminophenols at temperatures of about 200°-240° C.

Benzoxazoles which do contain nitro groups have been made by oxidative ring closure of corresponding Schiff bases, according to two papers by F. F. Stephens and J. D. Bower: *The Preparation of Benzimidazoles and Benzoxazoles From Schiff Bases; Parts I & II, J. Chem. Soc.*, 2971 (1949) and 1722 (1950). They reported obtaining 55-90% yields of the following benzoxazoles by oxidation of the corresponding Schiff bases with Pb(OAc)$_4$: 2-(p-nitrophenyl)-, 2-(m-nitrophenyl)-, 5-nitro-2-(p-nitrophenyl)-, 5-cyano-2-(p-nitrophenyl)-, 5-carbomethoxy-2-(2-hydroxy-4-nitrophenyl)- and 5-methyl-2-(p-nitrophenyl)-benzoxazole. The authors also reported recovering 2-(p-nitrophenyl)-benzoxazole in amounts which are equivalent to yields of about 72% and 50%, respectively, when chloranil and benzoyl peroxide were employed as oxidants instead of Pb(OAc)$_4$- which gave an 80% yield of the same benzoxazole. Other oxidants reported by Stephens and Bower as inactive or less effective for the preparation of 2-(p-nitrophenyl) benzoxazole are mercuric acetate, cupric acetate, sodium bismuthate, benzoquinone, N-bromosuccinimide, sulfuryl chloride and hydrogen peroxide/potassium ferricyanide.

Lead tetracetate was tested as an oxidant for preparation of the subject (nitro-substituted) benzoxazoles by the preceding method but was generally found to give multi-component reaction products and/or poor yields of the desired compounds. Similarly unsatisfactory results were obtained with both sulfuryl chloride and hydrogen peroxide. When benzoyl peroxide was used as the oxidant, the reaction was rapid but the results were highly variable, according to the specific Schiff base involved. Although good yields were obtained with the latter oxidant in a couple of instances, the results were generally not good enough to make the use of benzoyl peroxide — a relatively expensive oxidant — attractive for use in commercial manufacture of the subject benzoxazoles.

A need for a more efficient and economical method of preparing the above-described nitro-substituted benzoxazoles is thus apparent.

OBJECTS OF THE INVENTION

A primary object of the present invention is to provide an efficient and more economic method for preparing benzoxazoles.

A particular object is to provide an effective and economic method of preparing 2-(2-hydroxy-3 or 5-nitrophenyl) benzoxazoles by oxidation of corresponding Schiff bases.

An additional object is to provide a catalyst/oxidant combination which is relatively inexpensive and is capable of converting Schiff bases to benzoxazoles in high yields.

Still other objects will be made apparent to those skilled in the art by the following specifications and claims.

SUMMARY OF THE INVENTION

The present invention is the use of catalyst/oxidant combinations of a certain type for the oxidation of Schiff bases to benzoxazoles. More specifically, the invention may be defined as a method of preparing benzoxazoles of the formula:

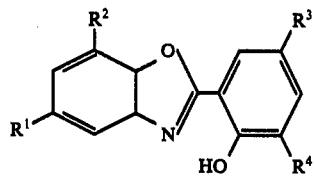

wherein one of $R^3$ and $R^4$ is $-NO_2$ and the other is $-H$, $-NO_2$ or alkyl of 1 to 20 carbons; and $R^1$ and $R^2$ are independently $-H$ or alkyl of 1 to 20 carbons, with the proviso that $R^1$, $R^2$, $R^3$ and $R^4$ contain a total of at least 6 carbons, said method comprising contacting a corresponding Schiff base of the formula

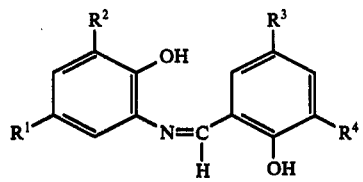

wherein $R^1$, $R^2$, $R^3$ and $R^4$ are as above defined, with a copper halide catalyst $CuX_n$, X being Br or Cl and n being 1 or 2, and with a peroxy compound of the formula $R^5-O-O-R^6$, in which $R^6$ is H or $R^5$ and $R^5$, independently in each occurence, is a hydrocarbyl group of 2 to 20 carbons and preferably 4 to 10 carbons, said contacting being effected by agitating a mixture of said Schiff base, said catalyst, said peroxy compound and an inert liquid, at a temperature of at least 25° C., for at least 5 minutes.

The invention may also be regarded as an improvement in the method of preparing benzoxazoles by oxidative ring-closure of correponding Schiff bases, derivable from the condensation of o-hydroxy anilines with salicylaldehydes, said improvement comprising employing as the oxidant the combination of a catalyst and a peroxy compound as above defined.

Preferably, the catalyst and the reactants are agitated with the medium at a temperature of at least 70° C., for at least 10 minutes.

DETAILED DESCRIPTION

The precursor Schiff bases, as above defined, are readily prepared in well known procedures by the spontaneous reaction of o-aminophenols and salicylaldehydes. Other known methods of making Schiff bases of course may be utilized, where suitable.

The peroxy compounds employed in the present process are well known materials. Methods of making these compounds and their pertinent properties are reviewed in: Kirk-Othmer, *Encyclopedia of Chemical Technology*, 2 d. ed., Vol. 14, pp 766–794 (1968).

The method of the invention is practiced by bringing together the Schiff base and the peroxy compound in the presence of the copper halide catalyst. At least enough of an inert medium is included so that the resulting mixture is a readily stirred solution or suspension at the reaction temperature to be employed. The copper halide catalyst will generally not be appreciably soluable in the liquid phase and agitation ordinarily will be essential to efficient utilization of the catalyst.

In referring to the reaction medium, the term inert is used herein to mean not detrimentally reactive, with any of the components of the reaction mixture, to an intolerable degree. Peroxy compounds are frequently capable, at least under free radical conditions, of abstracting a hydrogen from even such generally inert materials as linear alkanes. However, this does not mean that only compounds, such as $CCl_4$, which have no C—H groups, are suitable media for the reaction. Several of the common organic solvents, such as benzene, chloroform and chlorobenzene, for example, may be used for this purpose. Alcohols are generally less suitable and contact between peroxy compounds and carbonyl compounds — acetone in particular — should assiduously be avoided.

The lower alkyl hydroperoxides are soluble in water and so is cupric chloride. However, the precursor Schiff bases are generally insoluble in water and the use of water alone as the reaction medium is not indicated. On the other hand, a saturated solution of water in a water-immiscible solvent, such as benzene, chloroform or n-butanol may be a suitable reaction medium in some cases. This is particularly so when the Schiff base is highly soluble in the organic solvent, cupric chloride is used as the catalyst and a water soluble peroxy compound, such as t-butyl hydroperoxide, is used as the oxidant. (Dialkyl peroxides are generally not water soluble and may hydrolyze at the reaction temperatures contemplated.) When a solvent for water, such as t-butanol, is employed as the medium, the reaction mixture may contain a substantial amount of water, up to the point where the solubility of the Schiff base is decreased to an intolerable extent.

Although some of the benzoxazole will be formed at just about any reactant ratio, the amount of peroxy compound employed will ordinariy be at least sufficient to provide one —O—O— moiety per molecule of the Schiff base. That is, at least a stoichiometric amount of the peroxy compound will usually be introduced to the reaction mixture. In some instances, the use of greater amounts, up to about 110%, of stoichiometric, may be advantageously employed. Even more than a 10% excess of the peroxy compound may be used, but this will tend to result in an increased make of by-products and will increase the cost of the operation substantially.

In accordance with well known principles, it is desirable to establish the concentration of the peroxy compound at a relatively high initial level, in order to attain as high a reaction rate as possible. However, the amount of secondary reaction products may tend to increase as the concentration of the peroxy compound is increased. In the latter circumstance, it may be advantageous to add whatever excess of the peroxy compound is used at intervals as the reaction proceeds.

Care must also be taken to avoid the combination of an oxidizable reaction medium and a high oxidant concentration. Guidance in this respect is readily obtained by carrying out the reaction, on a very small scale, in a Differential Thermal Analysis (DTA) unit, at successively higher oxidant concentrations (and temperatures). Concentrations of 0.5 millimoles of the peroxy compound per 50 milliliters of solvent (0.1g mole liter of benzene) are considered well below hazardous levels and have been found to give generally satisfactory reaction rates. Higher levels may of course be checked out for any specific commercial application of the subject method.

Suitable temperatures for the oxidation range from the lowest temperature at which the reaction proceeds at a satisfactory rate to a temperature so high that thermal instability of the peroxy compound or secondary reactions becomes a problem, or the pressure required to maintain the reaction mixture in a liquid state becomes excessive. The reaction rate depends not only on the reactant ratio and temperature, but also on the specific Schiff base and the particular peroxy compound involved. Solvent effects may also influence the reaction rate. However, even the most facile oxidations observed would be expected to require contact times of up to 72 hours or more at a temperature of 25° C. and to require a contact time of at least 5 minutes at substantially elevated temperatures. It is preferred that contact be maintained for at least 10 minutes at a temperature of at least 70° C. In general, the reaction mixture should be agitated at a temperature of about 80° C. or more for at least an hour, in order to attain good yields of the benzoxazoles. However, contact times of less than an hour are advisable to minimize the amount of secondary or side reaction products formed, when the most facile oxidations are carried out at temperatures of 80° C. or more. In general, temperatures above about 200° C. do not appear to be advantageous and it is preferred to operate at temperatures below about 150° C.

It is highly preferred to operate at ordinary ambient pressures. However, the reaction may be carried out at subatmospheric pressure (provision being made for efficient condensation of evolved vapors to avoid volatility losses) or at supraatmospheric pressures at least equal to the autogenous pressure exerted by the reaction mixture at the contemplated reaction temperature.

The course of the reaction may readily be followed by periodically withdrawing samples of the reaction mixture and analyzing them by infra-red spectroscopy, thin layer chromatography, etc.

The reaction mixture may be worked up and the benzoxazole content thereof isolated, by any suitable technique. A convenient procedure is to filter out any undissolved catalyst, or other solids, and to wash the filtrand with diethyl ether, the wash being allowed to join the filtrate (assuming no substantial amount of unconsumed peroxy compound is present). The combined filtrate/wash is then repeatedly extracted with aqueous sulfuric acid until an extract is obtained which fails to give a positive test for copper with ammonium hydroxide. The organic phase is washed with water, then with salt brine, dried over anhydrous $Na_2SO_4$, filtered and stripped of volatiles under reduced pressure, as in a rotary evaporator.

Exemplary specific hydroperoxides which may be employed in the practice of the present invention are ethyl hydroperoxide, isopropyl hydroperoxide (b.p. 107°–109° C. at 760 mm Hg), t-butyl hydroperoxide (b.p. 35° C. at 17mm Hg), cyclohexyl hydroperoxide (b.p. "room temperature" at $10^{-4}$ mm Hg), cumene hydroperoxide b.p. 53° C. at 0.1 mm Hg), n-decyl hydroperoxide (b.p. 61°–3° C. at 0.3 mm Hg), 2,3-benzocyclohexyl hydroperoxide (b.p. 120°–5° C. at 0.2 mm Hg), and n-octadecyl hydroperoxide (m.p. 49°–50° C.).

Exemplary specific peroxides which may be employed in the practice of the invention are:
ethyl methyl peroxide (b.p. 40° at 740 mm Hg),
diethyl peroxide (b.p. 64° at 740 mm Hg),
t-butyl methyl peroxide (b.p. 23° at 119 mm Hg),
allyl t-butyl peroxide (b.p. 55° at 75 mm Hg).
di-sec-butyl peroxide (b.p. 59° at 50 mm Hg),
di-t-butyl peroxide (b.p. 111° at 760 mm Hg),
di-isoamyl peroxide (b.p. 54° at 5 mm Hg),
isopropyl 1-methylcyclohexyl peroxide (b.p. 28°–9° C. at 2.5 mm Hg),
t-butyl 4-methylbenzyl peroxide (b.p. 65° at 0.2 mm Hg),
di-n-heptyl peroxide (b.p. 38°–40° C. at 20 mm Hg),
bis ($\alpha,\alpha$ -dimethylbenzyl) peroxide (cumene peroxide; m.p. 39° C.),
t-butyl triphenylmethyl peroxide (m.p. 72°–73° C.),
di-n-hexadecyl peroxide (m.p. 44°–46° C.) and
bis-(triphenylmethyl) peroxide (m.p. 193° C.).

The preferred peroxy compounds for the subject oxidation are those of the formula $R^5$—O—O—$R^6$, as defined earlier herein, in which $R^6$ is H or $R^5$ and $R^5$ is an alkyl group of 4 to 10 carbons or a phenalkyl group of 7 to 10 carbons, independently in each occurrence. Particularly preferred among the latter class of peroxy compounds are those in which $R^5$ is a secondary or tertiary alkyl or phenalkyl radical. t-butyl radicals and cumene ($\phi$ C $(CH_3)_2$ — radicals are most preferred.

Suitable catalysts for the oxidation of the subject Schiff bases to the corresponding benzoxazoles with peroxy compounds are those of the formula $CuX_n$, wherein X is Br or Cl, independently, and $n$ is 1 or 2. Cuprous and cupric chloride are preferred catalysts for the reaction. The following specific peroxy compound/copper halide combinations are particularly preferred for the practice of the present invention: t-butyl hydroperoxide/CuCl, cumene hydroperoxide/CuCl and di-t-butyl peroxide/$CuCl_2$. The latter combination is most preferred.

The following examples are for purposes of illustration and are not to be construed as limiting the present invention in a manner inconsistant with the claims appended to these specifications.

EXAMPLES

Preparation of 2-(2-hydroxy-3-nitro-5-nonylphenyl)-5-t-butylbenzoxazole

1. Using t-butyl hydroperoxide (TBHP) in benzene with CuCl

The Schiff base intermediate was prepared by stirring and refluxing for 2 hours a mixture of 1.47g. (5 m moles) of 5-nonyl-3-nitrosalicaldehyde, 0.826g. (5 m moles) of 4-t-butyl-2-aminophenol and 50 ml of benzene. The water produced in the reaction was removed by use of a Dean-Stark water separator on which the reflux condenser was mounted. Analysis by TLC (Thin Layer Chromatography; on silica gel, eluted 1:4 with ethyl acetate and benzene), of samples taken periodically from the reaction mixture, showed that the reaction had been complete after the first hour of contact.

The base was oxidized in-situ as follows. To the stirred, cooled solution of the base was added 0.05 g. (0.5 m moles; 10 mole %) of CuCl and then a solution of 0.5 grams of 90% TBHP (5 m moles) in 5 ml. of benzene. The solution was stirred and refluxed at ~80° C. for an hour, the evolved water being removed as in the preceding reaction. (TLC analysis showed complete comsumption of the Schiff base in about 10 minutes). The reaction mixture was filtered by suction in a medium porosity sintered glass funnel, diluted with 30 ml. of diethyl ether and the resulting ethereal solution extracted in a separatory funnel with five 40 ml. portions of aqueous $H_2SO_4$ (150 g/liter). The last extract gave a negative test for copper with ammonia. The organic phase was then washed with five 40 ml. portions of water, followed by one wash with 50 ml. of saturated aqueous NaCl, dried 90 minutes over anhydrous $Na_2SO_4$ and filtered. The filtrate was stripped to a final kettle temperature of 90° C. under reduced pressure (0.1 mm Hg, final). A dark solid residue, identified as the title compound, 90% pure, by NMR (Nuclear Magnetic Resonance), was obtained in the amount of 2.13 g (equivalemt to 90% of the theoretical yield of the pure benzoxazole). The NMR $\delta$ values, in ppm, for this compound (M=438.57) are 0.5–2.0 (m, 28H, $CH_3$ $CH_2$), 7.0–8.5 (m, 5H aromatic H).

2. Using Cumene Hydroperoxide (CHP) in Benzene with CuCl

The Schiff base was prepared essentially as above and was stored (in-situ) at room temperature for 67 hours. 0.5 m moles each of CuCl and CHP (84.4% in benzyl alcohol) were then added and the resulting mixture was stirred and refluxed at ~80° C. for 3 hours, the evolved water being removed as formed by a Dean-Stark separator. TLC analysis showed a small amount of the Schiff base to be unconverted, so the reaction mixture was refluxed until the Schiff base was no longer detectable, a total of about 0.06 m moles more (~12% excess) of the oxidant being added in several increments. The total contact time for the oxidation was 5 hours. Worked up in the preceding manner, the reaction mixture gave 2.27 grams of a viscous dark oil of which (by NMR and simultaneous equation analysis) about 85–86% by weight was the title compound. This was equivalent to about 89% of the theoretical yield of the benzoxazole.

3. Using di-t-butyl Peroxide (DTBP) in Chlorobenzene with $CuCl_2$

The Schiff base was prepared essentially as above, but in chlorobenzene as the reaction medium, and was oxidized in situ as follows. To the cooled, stirred solution of the base was added 0.0679 grams (0.5 m moles) of anhydrous $CuCl_2$ (mixed with 3 ml of chlorobenzene and 0.735 g. (5.03 m moles) of DTBP. The mixture was stirred and refluxed at ~132° C. for 2 hours. (TLC analysis of a sample taken after a contact time of 1 hour showed no Schiff base left unconverted.) Worked up as above, the reaction mixture gave 2.01 grams (92% of the theoretical yield of the benzoxazole) of a dark viscous oil, identified (by NMR) as consisting essentially of the title compound.

4. Selective Copper Extraction

Reagent grade metal sulfate salts and sulfuric acid were used to prepare an aqueous stock solution that contained about 1 gram/liter each of copper and ferric iron at pH 2. Ten ml aliquots of this stock solution were pipetted into several small bottles and two ml of either dilute sulfuric acid, water, or dilute sodium carbonate solution were added to give a final aqueous volume of 12 ml and an initial pH in the range of 1.7 to 2.7. Four ml of an approximately 0.1 molar solution of the 2-(2-hydroxy-3-nitro-5-nonylphenyl)-5-t-butylbenzoxazole in toluene were then pipetted into all but one ("feed") of the sample bottles which were then placed on a mechanical shaker and vigorously mixed for 30 minutes. The two phases were carefully separated, the equilibrium pH of the aqueous phase was measured, and the copper and iron concentation of the aqueous phase determined by atomic absorption spectrometry. The percent of metal extracted under these conditions was calculated from the difference between the feed and equilibrium aqueous concentrations. The results of these tests are shown in Table I.

TABLE I

| Sample | Equil. pH | Aqueous Conc(ppm) | | Percent Extracted | |
|---|---|---|---|---|---|
| | | $Cu^{2+}$ | $Fe^{3+}$ | $Cu^{2+}$ | $Fe^{3+}$ |
| Feed | 2.18 | 838 | 768 | — | — |
| 1 | 1.64 | 574 | 764 | 32 | 1 |
| 2 | 1.92 | 405 | 730 | 52 | 5 |
| 3 | 2.19 | 302 | 764 | 64 | 1 |

The relatively high iron extraction from feed #2 is believed to be an artifact arising from experimental error. In any event, the copper to iron selectivity ratio was at least 10 at this intermediate pH and was 32 and 64 at the lower and higher pH's of feeds #1 and #3.

The loaded extracts obtained from such feeds in the preceding manner are readily stripped with dilute mineral acid solution having a pH of about 1.

What I claim is:

1. The method of preparing benzoxazoles of the formula

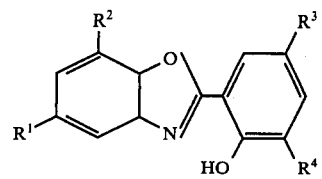

wherein one of $R^3$ and $R^4$ is —NO2 and the other is —H, —NO2 or alkyl of 1 to 20 carbons and $R^1$ and $R^2$ are independently —H or alkyl of 1 to 20 carbons, with the proviso that $R^1$, $R^2$, $R^3$ and $R^4$ contain a total of at least 6 carbons, said method comprising contacting a corresponding Schiff base of the formula

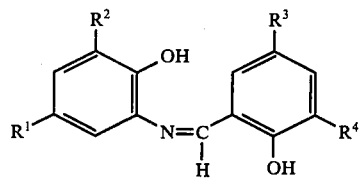

wherein $R^1$, $R^2$, $R^3$ and $R^4$ are as above defined, with a copper halide catalyst $CuX_n$, X being Br or Cl and n being 1 or 2, and with a peroxy compound of the formula $R^5$—O—O—$R^6$, in which $R^6$ is H or $R^5$ and $R^5$, independently, in each occurrence, is a hydrocarbyl group of 2 to 20 carbons, said contacting being effected by agitating a mixture of said Schiff base, said catalyst, said peroxy compound and an inert liquid, at a temperature of at least 25° C., for at least 5 minutes.

2. The method of claim 1 in which said temperature is at least 70° C. and the contact time is at least 10 minutes.

3. The method of claim 2 in which said temperature is less than about 150° C.

4. The method of claim 1 in which the reaction mixture is refluxed and the evolved water is removed therefrom as formed.

5. The method of claim 1 in which said catalyst is cuprous or cupric chloride.

6. The method of claim 1 in which $R^5$ is an alkyl group of 4 to 10 carbons or a phenalkyl group of 7 to 10 carbons, independently in each occurrence.

7. The method of claim 6 in which said alkyl or phenalkyl group is a secondary or tertiary radical.

8. The method of claim 7 in which said radical is a t-butyl or $\phi C(CH_3)_2$— radical.

9. The method of claim 5 in which the cataylst is cuprous chloride and the peroxy compound is t-butyl hydroperoxide or cumene hydroperoxide.

10. The method of claim 5 in which the catalyst is cupric chloride and the peroxy compound is di-t-butyl peroxide.

* * * * *

UNITED STATES PATENT AND TRADEMARK OFFICE
CERTIFICATE OF CORRECTION

PATENT NO. : 4,120,862
DATED : October 17, 1978
INVENTOR(S) : Donald N. Brattesani It is certified that error appears in the above-identified patent and that said Letters Patent are hereby corrected as shown below:

Title should read "USE OF COPPER HALIDE CATALYSTS AND CERTAIN PEROXY COMPOUNDS TO OXIDIZE NITRO-SUBSTITUTED SCHIFF BASES TO BENZOXAZOLES".

Column 3, line 9, "corresponding" spelled incorrectly.

Column 4, line 5, "ordinarily" spelled incorrectly.

Column 6, line 33, "consumption" spelled incorrectly.

Column 6, line 48, "equivalent" spelled incorrectly.

Column 7, line 37, "concentration" spelled incorrectly.

Column 8, line 54, "catalyst" spelled incorrectly.

Signed and Sealed this

Twenty-fourth Day of April 1979

[SEAL]

Attest:

RUTH C. MASON
Attesting Officer

DONALD W. BANNER
Commissioner of Patents and Trademarks